United States Patent [19]

Mundell

[11] Patent Number: 4,506,681

[45] Date of Patent: Mar. 26, 1985

[54] SURGICAL IMPLANT

[75] Inventor: Peter J. Mundell, Verwoerdburg, South Africa

[73] Assignee: South African Inventions Development Corporation, Pretoria, South Africa

[21] Appl. No.: 436,705

[22] Filed: Oct. 26, 1982

[30] Foreign Application Priority Data

Nov. 11, 1981 [ZA] South Africa ............... 81/7811

[51] Int. Cl.³ .................... A61F 1/00; A61F 5/04
[52] U.S. Cl. ................... 128/92 D; 3/1.9; 3/1; 128/92 C
[58] Field of Search ........... 128/92 B, 92 BA, 92 D, 128/82, 82.1, 83, 92 G

[56] References Cited

U.S. PATENT DOCUMENTS

| 4,029,091 | 6/1977 | von Bezold et al. | 128/92 D |
|---|---|---|---|
| 4,170,990 | 11/1979 | Baumgart et al. | 128/92 D |
| 4,187,558 | 2/1980 | Dahlen et al. | 3/1 B |
| 4,329,748 | 5/1982 | Alexander et al. | 3/1 |

FOREIGN PATENT DOCUMENTS

| 2920223 | 11/1980 | Fed. Rep. of Germany ... 128/92 G |
|---|---|---|
| 629153 | 9/1949 | United Kingdom . |
| 646823 | 11/1950 | United Kingdom . |
| 841779 | 7/1960 | United Kingdom . |
| 1414303 | 11/1975 | United Kingdom . |

OTHER PUBLICATIONS

The Use of Semi-Rigid Carbon-Fibre Reinforced Plastic Plates for Fixation of Human Fractures, Tayton et al. in the Journal of Bone and Joint.
Surgery, vol. 64B, No. 1, 1982 at pp. 105 to 111.
Current Concepts of Internal Fixation of Fractures, H. K. Uhthoff, ed., Springer-verlag, Berlin, 1980, pp. 136-145.
Carbon Fibre Reinforced Epoxy as a High Strength, Low Modulus Material for Internal Fixation Plates, by Bradley et al. in Biomaterials, vol. 1, pp. 38-40.
Internal Fracture Fixation with Partially Degradable Plates, by Alexander et al. In Press, Proceedings Northeast Bioengineering Conference, 1981.

Primary Examiner—Richard J. Apley
Assistant Examiner—D. J. Isabella
Attorney, Agent, or Firm—Ladas & Parry

[57] ABSTRACT

A precursor device is provided for forming a surgical implant for prosthetic surgery. The device has a body or matrix of biocompatible material which is thermoplastic and electrically insulating. Embedded in the matrix is a plurality of electrically conductive fibres. Opposite ends of at least some of the fibres project outwardly from the matrix to permit heating and softening of the matrix for shaping thereof, by the application of a suitable electric potential to opposite ends of said outwardly projecting fibres.

13 Claims, 7 Drawing Figures

SURGICAL IMPLANT

This invention relates to surgical implants. More particularly, the invention relates to a precursor device from which a surgical implant is formed.

According to the invention, a precursor device for forming a surgical implant comprises a matrix of biocompatible thermoplastic electrically insulating material within which is embedded a plurality of electrically conductive fibres, opposite ends of at least some of the fibres projecting outwardly from the matrix to permit heating and softening of the matrix for shaping thereof, by the application of a suitable electric potential to opposite ends of said outwardly projecting fibres.

The precursor device may typically be for a surgical implant such as a bone plate or intramedullary nail. In use, it is often desirable to have such implants shaped so that they can extend along a path which is not necessarily straight, but which may be somewhat curved to permit them to conform more or less closely with the shape of the part of the body, human or animal, for which they are intended, e.g. to extend along the surface or interior of a bone which is not necessarily straight.

The biocompatible material of the matrix may be a suitable resin, such as a polysulphone or polylactic acid. In some cases, polylactic acid may be preferred, as it is biodegradable, thereby permitting the implant to be left indefinitely in place. Thus, the biocompatible material of the matrix may be biodegradable, being capable of eventual, at least partial, absorption and excretion by a body in which it is implanted, while being replaced by invasive bodily tissue.

The fibres, particularly when the matrix is biodegradable, should preferably also be of a biocompatible material, i.e. one which is inert or gives rise to no undesirable reactions when in contact with bodily fluids. Carbon fibres are suitable for this purpose, being inert in the body while providing excellent mechanical reinforcing of the matrix and adequate conductivity for heating.

As is the case of bone plates and intramedullary nails, the implants and hence the precursor devices will often be elongated, and in such cases the outwardly projecting opposite ends of the fibres may conveniently project out of opposite ends of the matrix in bundles. Where they project from the matrix, they may be enclosed by sleeves, e.g. of heat-shrunk plastics material to hold them together in easily manageable bundles for easy attachment to an electric power source. In use, the parts of the precursor devices from which the fibres project, or at least the outwardly projecting parts of the fibres, will be removed after the shaping from the precursor device together with the sleeves, to leave the final implant, shaped and ready for use.

As mentioned above, the fibres may act to reinforce the matrix as well as heat it, being located in the matrix to extend along paths in positions and in directions which permit both effective heating of the matrix and effective reinforcing in use of the eventual implant by the fibres.

The invention extends to a method of making a device as described above, which comprises locating a plurality of electrically conductive fibres in a mould so that opposite ends of at least some of the fibres project outwardly from the mould, and causing or allowing a biocompatible thermoplastic electrically insulating material to set in the mould to form a matrix in which the fibres are embedded and from which said outwardly projecting fibre ends project.

Molten matrix material may be injected into the mould after the fibres have been located in the mould. Instead, matrix material in particulate form may be introduced into the mould together with the fibres, being melted in situ prior to its being caused or allowed to set. Instead, prior to the moulding, one or more layers of the fibres may be impregnated with matrix material, the said layer or layers then being heated under pressure in the mould to melt the matrix material in situ, before the matrix material sets, to cause the layers to adhere together to form the device.

Locating the fibres in the mould may be so that they extend along paths in positions and in directions which permit both effective heating of the matrix and effective reinforcing in use of the eventual implant by the fibres.

An elongated matrix having said outwardly projecting opposite ends of the fibres projecting from opposite ends thereof may be formed, the method including the step of gathering said outwardly projecting fibre ends into two bundles, one at each end of the matrix.

In use, prior to implanting the device, the matrix will be heated, as mentioned above, by means of an electric potential applied to said opposite ends of the outwardly projecting fibres to soften the matrix, the matrix then being shaped while soft, into a desired shape for its intended use, and the device being implanted after it has been caused or allowed to harden in said desired shape, and after the outwardly projecting fibres and, if necessary, parts of the matrix have been removed to provide the eventual implant.

As an initial step, an incision may be made in the body into which the implant is to be implanted to expose the intended site of the implant, after which the matrix is shaped and one or more parts of the device are removed to provide an implant which fits said site.

The matrix may be shaped by hand, its fit being estimated by eye, the device then being cooled and located in situ in its intended site, at least once, to test its fit before the fibres are removed and the implant is implanted. Instead, a template may be inserted into the intended site of the implant and shaped to correspond with the intended shape of the implant, the template then being removed from the site and the matrix being shaped with reference to the template to provide the matrix with the required shape.

The invention will now be described, by way of example, with reference to the accompanying diagrammatic drawings, in which FIG. 1 shows a plan view of a device according to the invention;

In the various Figures of the drawings, the same reference numerals designate the same parts unless otherwise specified.

Figure 1:
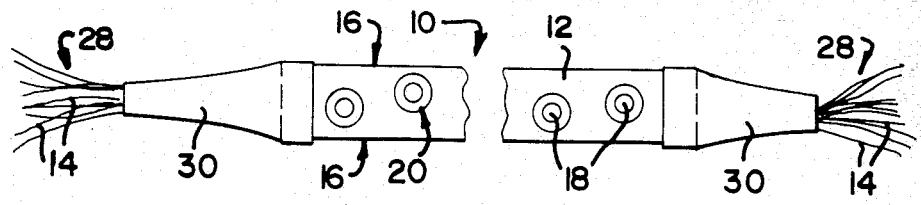

In FIG. 1 of the drawings, reference numeral 10 generally designates a precursor device for forming a surgical implant in the form of a bone plate. The device comprises a body 12 in the form of a flattened elongated plate of biocompatible electrically insulating thermoplastic material, which forms a matrix wherein is embedded a plurality of carbon fibres 14, of the type typically having a diameter of about 0.008 mm.

The body 12 is substantially flat and straight, having parallel longitudinal side edges 16, and two series of equally spaced holes 18 extending along its length, the holes of the one series being staggered relative to the holes of the other series, and each series being adjacent one of the side edges, but it will be appreciated that in smaller plates, a single series of holes can be used.

The holes are intended for studs whereby the eventual bone plate (17 in FIG. 2) will be attached to a bone, and are thus countersunk as at 20 on one side of the body 12. On the other side of the body 12, the bone plate has two longitudinally extending ribs 22, along its side edges 16, to aid in seating of that side of the body 12 against a bone.

The device 10 is formed (see FIG. 3) by winding and laying down a plurality of skeins or tows 24 of carbon fibres 14 around a plurality of pins or pegs 26 in a mould. The tows 24 can be wound according to any suitable arrangement whereby they are arranged to extend in directions, and to be located in positions where they will best, or at least sufficiently, serve to resist or combat anticipated stresses during use, and where they will provide for at least effective dispersion of heat throughout the matrix, as described hereunder. A suitable arrangement for one tow is shown in FIG. 3.

Figure 3:
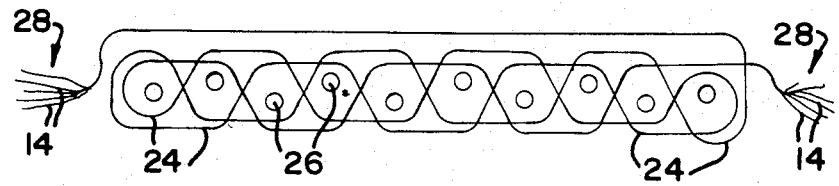
FIG. 3 shows a detail of the interior of the implant of FIG. 2.

The tow 24 shown in FIG. 3 can start to be laid down at either of its ends 28, to finish at its opposite end 28. Several tows are laid down on top of each other, and they can follow similar but different paths, e.g. starting at the other end of the mould, so that each tow does not only criss-cross itself, but criss-crosses the adjacent tows, so that the tows together form an effective reinforcing and heating medium.

When sufficient, say 3, tows have been laid in position, the matrix material can then be injected into the mould in molten form, or introduced as a powder into the mould and melted in situ, and allowed to cool and harden, the pegs 26 forming the openings 18. The ends of the tows will project, as shown at 28, from the ends of the mould, and will be clamped these to prevent molten matrix from running out of the ends of the mould.

When the matrix has set, the device is removed from the mould, and sleeves 30 are shrink-wrapped around the ends of the body 12, where the tows project from the body, to retain the fibres 14 in bundles as at 28 in FIG. 1, which can easily be dealt with.

It should be appreciated that the pattern shown in FIG. 3 is merely representative, and any desired pattern which is effective for reinforcing and heating can be used to lay down the tows, provided that their ends 28 project from the ends of the mould, as shown in FIG. 3.

Figure 4:
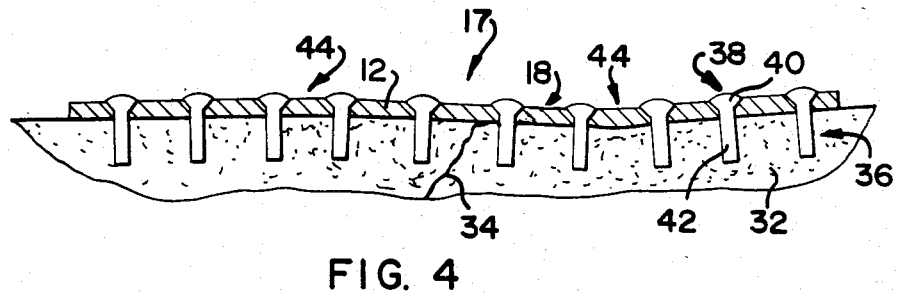
FIG. 4 shows a sectional side elevation of the implant of FIG. 2 in use.

In use, e.g. in the repair of a broken femur 32 as shown in FIG. 4, it will often be found that the femur 32 is not necessarily straight, and as femurs can be of different shapes and sizes, it is unproductive to have different shapes and sizes for the body 12 of the bone plate. The device 10 of FIG. 1 is thus shaped and bent to conform with the bone 32.

In use, the bone 32, e.g. having a diagonal break 34, is exposed and the bone portions are arranged so that they abut in the correct relationship and alignment at the break at 34.

The bundles of fibres 28 are then connected to the output terminals of a suitable electrical power source, such as a transformer, and sufficient potential and current are applied to the fibres 14 to heat them and the matrix 12 sufficiently to soften the matrix. The surgeon will then grip the body 12, e.g. with suitable hand-held clamps, tongs or the like, and will shape and bend the body 12 by eye, until it conforms in shape with the bone 32 so that it can be laid against the bone to follow and abut the outer surface of the bone against which it is laid, as closely as possible. During the shaping, the device can be cooled from time to time by dipping it in a saline solution, and can be placed against the bone to see how good the fit is. Instead, a flexible template can be used, the template being shaped to have a curvature corresponding to that of the bone, and the device being compared with the template to determine the fit.

Figure 2:
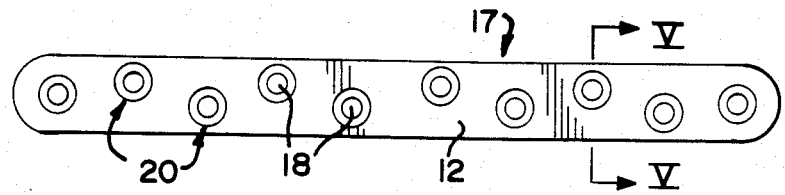
FIG. 2 shows a plan view of an implant formed from the device of FIG. 1.

When an adequate fit has been obtained, the ends of the device 10 are cut by means of suitable cutters, to form the bone plate 17 shown in FIG. 2 and FIG. 4, and the bone plate is then attached to the bone by drilling suitable holes 36 in the bone registering with the holes 18, and by using suitable bone screws, or, as shown, studs 38 having heads 40 and expandable shanks 42 to hold the bone plate in position. The shanks 42 are expanded in the holes 36 to grip the bone 32, the heads 40 being received at 20 in the body 12 of the bone plate, where the holes 18 are countersunk.

The side of the bone plate having the ribs 22 is that which abuts the bone 32, and it can be seen from FIG. 4 that where the bone changes shape or direction as at 44, the bone plate is correspondingly shaped to abut against the bone. This would be impossible were the bone plate to be straight.

Further aspects of the invention are that the holes 18 can be dispensed with, and the surface of the bone plate having the countersunk mouths at 20 to the holes 18 can be provided with a plurality of longitudinally spaced bosses, ribs, or grooves.

With this embodiment, several narrower bone plates can be placed alongside the bone 32, spaced laterally from one another, and can be held in position by suitable plastics straps. This can provide for better access of oxygen, blood and other bodily fluids to the bone, and these bone plates will usually be provided over a sector of the circumferential periphery of the bone, when seen in cross-section, the remainder of the bone being undisturbed, except for the straps which extend circumferentially around the bone and bone plates to hold the bone plates in position.

The straps, like the studs 38, may be made of some suitable biocompatible and possibly biodegradable material.

Another way of making the device of FIG. 1, is by impregnating the matrix material into one or more layers of the fibres, and heating the layers together in a mould to melt the matrix material under pressure in the mould to form the device. Thus, for example, the layers of fibres can be saturated with a saturated solution of polysulphone in a suitable solvent such as N-methyl pyrrolidone-2, after which the solvent can be evaporated at a suitable temperature (for N-methyl-pyrrolidone-2, 100° C. is suitable) to leave the layers impregnated with the solid thermoplastic Solute residue, ready for heating in the mould.

Figure 6:
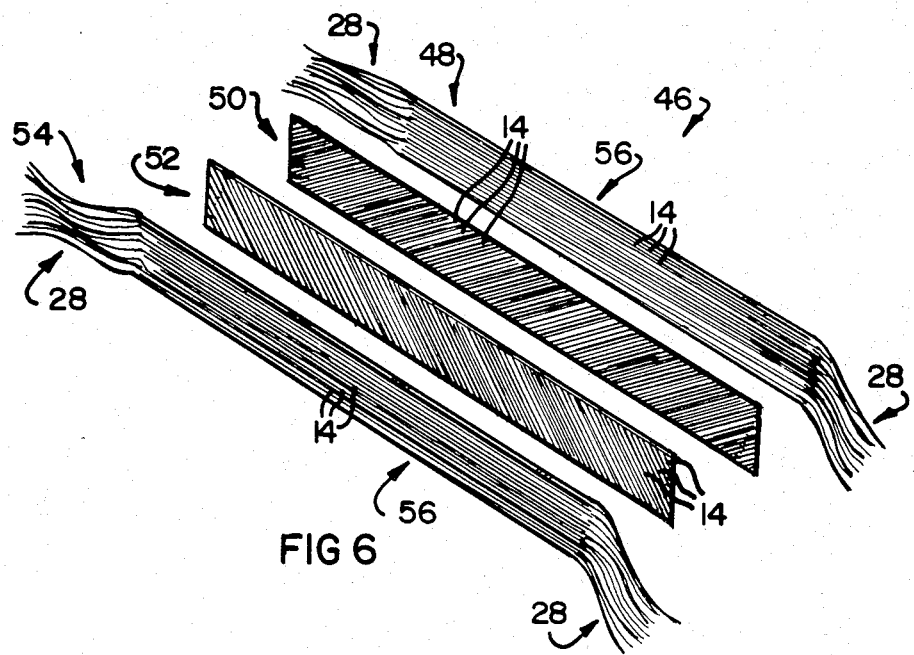
FIG. 6 shows an exploded three-dimensional view of a device according to FIG. 1 during manufacture thereof.

In FIG. 6, reference numeral 46 generally designates a device of this type during manufacture. An exploded view is shown, comprising four layers of carbon fibres designated 48 to 54 respectively. Layers 48 and 54 are identical and comprise body portions 56 which are elongate rectangular, having the same outline as the body 12 of FIG. 1. These body portions comprise a multiplicity of essentially parallel carbon fibres 14 which have been impregnated with matrix material and dried as described above, the matrix material causing the fibres to adhere together. At opposite ends of the body portion 56 the fibres 14 are not impregnated and will form the bundles 28 of FIG. 1. These layers 48 and 54 can conveniently be cut from larger sheets of pre-impregnated parallel carbon fibres which have strips of unimpregnated fibres along opposite edges at the ends of the fibres, the cuts being parallel to the fibres.

Figure 5:
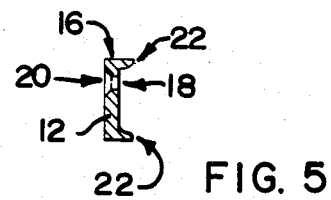
FIG. 5 shows a cross-section, along line V—V in FIG. 2 of the implant of FIG. 2.

The layers 50 and 52 have the same outline as the body portions 56 of the layers 48 to 54, and are cut from similar sheets of pre-impregnated carbon fibres in a similar fashion, except that the cuts are at an angle to the direction of the fibres of about 40°–45°. The layers 48 to 54 are assembled together as shown in FIG. 5, with the layers 48 and 54 outermost, and the layers 50 and 52 sandwiched therebetween with their fibres extending diagonally or at an inclination relative to the fibres of the layers 48 and 54, and in opposite directions, so that the fibres of the layers 50 and 52 criss-cross, and also criss-cross the fibres of the layers 48 and 54.

The layers 48 to 54 typically have a thickness of about 0.5-2 mm, and as many as are necessary are used, the four shown in FIG. 6 being merely illustrative. However, two layers of the type 50, 52, with their fibres criss-crossing, should always be sandwiched between a pair of layers of the type 48, 54, and layers of the type 48, 54 will typically be outermost in the eventual laminate. Naturally, if desired, layers of the type 50,52 can be omitted, and it will be appreciated that they function only for mechanical reinforcing, the layers 48, 54 acting in use to heat the matrix as well as to provide strength.

The layers 48 to 54 are sandwiched in the order described above, in the mould with the fibre ends at 28 projecting out of the mould and are then heated under a suitable pressure and temperature (e.g. 300° C. for polysulphone) to cause the matrix material to melt and, after cooling and setting, to stick the layers together to form a unitary body 12. The sleeves 30 may then be applied as described above.

Figure 7:
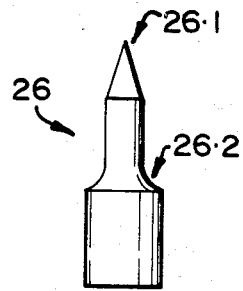
FIG. 7 shows a side elevation of a pin used in the manufacture of the device of FIG. 1.

To form the holes 18 (see FIG. 1), after heating and before final pressing, pegs or pins 26 of the type shown in FIG. 7 are inserted into the mould at the desired positions to form the holes. From FIG. 7 it will be seen that these pins have points 26.1 for easy insertion through the sandwich of layers with no more than marginal damage to the fibres 14 which are pushed aside during insertion, and the pins 26 have tapered roots or bases 26.2 for forming the countersinking at 20 (see FIG. 1). Similar pins 26 may be used for the method of manufacture described with reference to FIG. 3, although the points 26.1 are not needed in that case.

The invention provides the advantage that a surgical implant precursor is provided which can easily be shaped in situ for a close fit in position in a body undergoing surgery, e.g. to fit against a bone being repaired.

I claim:

1. A precursor device for forming a surgical implant in the form of a bone prothesis which comprises a stiff moldable matrix of biocompatible thermoplastic electrically insulating material which material has sufficient rigidity for supporting bone in carrying out a load bearing function and within which is embedded a plurality of electrically conductive fibres, opposite ends of at least some of the fibres extending outwardly from the matrix and being exposed to provide electrical contacts which permit heating and softening of the matrix for shaping thereof, by the application of a suitable electric potential to said contacts.

2. A precursor device as claimed in claim 1, in which the biocompatible material of the matrix is a material selected from the group consisting of polysulphone and polylactic acid.

3. A precursor device as claimed in claim 1, in which the biocompatible material of the matrix is biodegradable, and is capable of eventual at least partial absorption and excretion by a body in which it is implanted, while being replaced by invasive bodily tissue.

4. A precursor device as claimed in claim 1, in which the fibres are biocompatible.

5. A device as claimed in claim 4, in which the fibres are carbon fibres.

6. A precursor device as claimed in claim 1, in which the matrix is elongated, and in which opposite ends of the outwardly projecting fibres project out of opposite ends of the matrix where they can be gathered together in bundles.

7. A device as claimed in claim 6, in which the outwardly projecting ends of the fibres, at opposite ends of the matrix, are gathered together in bundles, by sleeves which are shrunk-fitted around opposite ends of the matrix and around the outwardly projecting fibres, said fibres projecting outwardly from the sleeves to provide the contacts and the ends of the matrix, with their associated sleeves and outwardly projecting fibres, being disposable prior to implantation.

8. A device as claimed in claim 1, in which the fibres act to reinforce the matrix and are located in the matrix to extend along predetermined paths in positions and in directions which permit both effective heating and reinforcing of the matrix to provide a proper bone support structure.

9. A method of prosthetic surgery in which a bone prosthesis comprising a stiff matrix of biocompatible thermoplastic electrically insulating material within which is embedded a plurality of electrically conductive fibres, projecting outwardly from opposite ends of the matrix and being exposed to provide electrical contacts, is implanted in a living body, the method comprising, heating the matrix by means of an electrical potential applied to said electrical contacts to soften the matrix, shaping the matrix while soft into a desired permanent shape for its intended use, causing or allowing the matrix to cool and harden into said permanent shape, and then implanting the prosthesis into the body.

10. A method as claimed in claim 9, in which, as an initial step, an incision is made in the body where the prosthesis is to be implanted to expose the intended site of the prosthesis, after which the matrix is shaped with reference to said site to provide a prosthesis which fits said site.

11. A method as claimed in claim 10, in which the matrix is shaped by hand and its fit is estimated by eye, the prosthesis after being shaped and cooled, being located in situ in its intended site, at least once, to test its fit while it is in a condition to be heated and shaped again to improve its fit, before the prosthesis is implanted and the incision closed.

12. A method as claimed in claim 10, in which a template is inserted into the intended site of the prosthesis and shaped to correspond with the intended shape of the prosthesis, the template being removed from the site and the matrix being shaped with reference to the template to provide the matrix with the required shape.

13. A method as claimed in claim 9, in which the electrical contacts of the prosthesis are provided by having said opposite ends of the fibres project outwardly from the matrix, the method including removing at least said outwardly projecting fibres from the prosthesis after the prosthesis has been shaped into its permanent shape and before it is implanted into the body.

* * * * *